(12) United States Patent
Barber

(10) Patent No.: US 11,521,710 B2
(45) Date of Patent: Dec. 6, 2022

(54) USER INTERFACE, SYSTEM, AND METHOD FOR COHORT ANALYSIS

(71) Applicant: Tempus Labs, Chicago, IL (US)

(72) Inventor: Mathew Barber, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 643 days.

(21) Appl. No.: 16/671,165

(22) Filed: Oct. 31, 2019

(65) Prior Publication Data

US 2020/0135303 A1  Apr. 30, 2020

Related U.S. Application Data

(60) Provisional application No. 62/753,504, filed on Oct. 31, 2018.

(51) Int. Cl.
| | |
|---|---|
| G06K 9/62 | (2022.01) |
| G16B 45/00 | (2019.01) |
| G16B 25/10 | (2019.01) |
| G16H 20/00 | (2018.01) |
| G16H 10/60 | (2018.01) |

(52) U.S. Cl.
CPC ........... *G16B 45/00* (2019.02); *G06K 9/6218* (2013.01); *G16B 25/10* (2019.02); *G16H 10/60* (2018.01); *G16H 20/00* (2018.01)

(58) Field of Classification Search
CPC .... G16H 10/60; G06K 9/6218; G06K 9/6215; G06K 9/6201
See application file for complete search history.

(56) References Cited

U.S. PATENT DOCUMENTS

| | | | |
|---|---|---|---|
| 2010/0130873 A1* | 5/2010 | Yuen | A61B 5/1126 600/595 |
| 2014/0067483 A1* | 3/2014 | Jeong | G06Q 10/06393 705/7.39 |
| 2016/0085910 A1 | 3/2016 | Bruand | |
| 2018/0268937 A1 | 9/2018 | Spetzler | |
| 2019/0087540 A1* | 3/2019 | Jung | G16H 50/70 |

(Continued)

OTHER PUBLICATIONS

Bailey, P., et al. "Genomic analyses identify molecular subtypes of pancreatic cancer." Nature 531.7592 (2016): 47.

(Continued)

*Primary Examiner* — Benyam Haile
(74) *Attorney, Agent, or Firm* — Quarles & Brady LLP

(57) ABSTRACT

A system and method that receive a distance matrix for multiple patients and a patient of interest, assign a radial distance value between the patient of interest and the other patients based on the distance matrix value for each of the multiple patients, generate an angular distance value between the multiple patients based at least in part on a measure of similarity between each patient, and minimize a cost function based at least in part on the angular distance value between each patient and each other patient. Minimizing the cost function may include calculating a patient contribution to the cost function for a plurality of angular distance values and selecting the angular distance value with the smallest patient contribution. The processor also may be configured to generate and display a radar plot based on the assigned radial distance value and generated angular distance value of each patient.

19 Claims, 12 Drawing Sheets

(56) References Cited

U.S. PATENT DOCUMENTS

2020/0051696 A1* 2/2020 Zhao ............... G16H 10/60

OTHER PUBLICATIONS

Cancer Genome Atlas Network. "Comprehensive molecular portraits of human breast tumours." Nature 490.7418 (2012): 61.
Dey, K. K., et al. "Clustering RNA-seq expression data using grade of membership models." bioRxiv (2016): 051631.
U.S. Appl. No. 16/657,804.
U.S. Appl. No. 62/882,466.
Austin, P. The use of propensity score methods with survival or time-to-event outcomes: reporting measures of effect similar to those used in randomized experiments, Stat Med. Mar. 30, 2014; 33(7): 1242-1258.
Ayers, M, et al. "IFN-?-related mRNA profile predicts clinical response to PD-1 blockade." The Journal of clinical investigation 127.8 (2017): 2930-2940.
Bray, F., et al. "Global cancer statistics 2018: GLOBOCAN estimates of incidence and mortality worldwide for 36 cancers in 185 countries." CA: a cancer journal for clinicians 68.6 (2018): 394-424.
Bray, N. L., et al. "Near-optimal probabilistic RNA-seq quantification." Nature biotechnology 34.5 (2016): 525.
Clinical Trial NCT03051035, First-in-Human Study of KO-947 in Non-Hematological Malignancies, posted Feb. 13, 2017.
Cseh B, et al. "RAF" neighborhood: protein-protein interaction in the Raf/Mek/Erk pathway. FEBS Lett. 2014;588:2398-2406.
Dienstmann, R., et al. "Database of genomic biomarkers for cancer drugs and clinical targetability in solid tumors." Cancer discovery 5.2 (2015): 118-123.
Dobin, A., et al. "STAR: ultrafast universal RNA-seq aligner." Bioinformatics 29.1 (2013): 15-21.
Faust, G. G., et al. "SAMBLASTER: fast duplicate marking and structural variant read extraction." Bioinformatics 30.17 (2014): 2503-2505.
Kitano, A., et al. "Tumour-infiltrating lymphocytes are correlated with higher expression levels of PD-1 and PD-L1 in early breast cancer." ESMO open 2.2 (2017): e000150.
Knight T, et al. Ras/Raf/MEK/ERK pathway activation in childhood acute lymphoblastic leukemia and its therapeutic targeting. Front Oncol. 2014;4:160.
Layer, R. M., et al. "LUMPY: a probabilistic framework for structural variant discovery." Genome biology 15.6 (2014): R84.
Li, H., et al. "Fast and accurate long-read alignment with Burrows-Wheeler transform." Bioinformatics 26.5 (2010): 589-595.
Liao, Y., et al. "featureCounts: an efficient general purpose program for assigning sequence reads to genomic features." Bioinformatics 30.7 (2013): 923-930.
Mclaughlin, J., et al. "Quantitative assessment of the heterogeneity of PD-L1 expression in non-small-cell lung cancer." JAMA oncology 2.1 (2016): 46-54.
Newman, A. M. et al. Robust enumeration of cell subsets from tissue expression profiles. Nat. Methods 12, 453-7 (2015).
Richards, S. et al. Standards and guidelines for the interpretation of sequence variants: a joint consensus recommendation of the American College of Medical Genetics and Genomics and the Association for Molecular Pathology. Genet. Med. 17, 405-24 (2015).
Robinson, D. R. et al. Integrative clinical genomics of metastatic cancer. Nature 548, 297-303. 2017.
Rooney, M. S., et al. Molecular and Genetic Properties of Tumors Associated with Local Immune Cytolytic Activity. Cell 160, 48-61 (2015).
Rosenbaum, P. R., et al. "The central role of the propensity score in observational studies for causal effects." Biometrika 70.1 (1983): 41-55.
Rubinsteyn, A., et al. "Predicting peptide-MHC binding affinities with imputed training data." BioRxiv (2016): 054775.
Stuart, E. Matching methods for causal inference: a review and a look forward, Statistical Science (2010) 25(1):1-21.
Szolek, A, et al. "OptiType: precision HLA typing from next-generation sequencing data." Bioinformatics 30.23 (2014): 3310-3316.
Teng, MWL, et al. "Classifying cancers based on T-cell infiltration and PD-L1." Cancer research 75.11 (2015): 2139-2145.
Vassilakopoulou, M., et al. "Evaluation of PD-L1 expression and associated tumor-infiltrating lymphocytes in laryngeal squamous cell carcinoma." Clinical Cancer Research 22.3 (2016): 704-713.
Velcheti, V., et al. "Programmed death ligand-1 expression in non-small cell lung cancer." Laboratory investigation 94.1 (2014): 107.
Wei, S.C., et al. "Fundamental mechanisms of immune checkpoint blockade therapy." Cancer discovery 8.9 (2018): 1069-1086.
Wimberly, H. et al. "PD-L1 expression correlates with tumor-infiltrating lymphocytes and response to neoadjuvant chemotherapy in breast cancer." Cancer immunology research 3.4 (2015): 326-332.

* cited by examiner

|  | Gene A | Gene B | Gene C | Gene D | Gene E | Gene F | ... |
|---|---|---|---|---|---|---|---|
| Patient 1 | 1 | 0 | 0 | 1 | 1 | 1 | |
| Patient 2 | 1 | 0 | 0 | 1 | 1 | 0 | |
| Patient 3 | 1 | 0 | 1 | 0 | 0 | 0 | |
| Patient 4 | 0 | 1 | 0 | 0 | 0 | 0 | |
| Patient 5 | 1 | 1 | 0 | 0 | 0 | 0 | |
| ... | | | | | | | |

|  | Gene A | Gene B | Gene C | Gene D | Gene E | Gene F | ... |
|---|---|---|---|---|---|---|---|
| Importance score | 0.8 | 0.1 | 0.15 | 0.4 | 0.1 | 0.6 | |

| | Patient 1 | Patient 2 | Patient 3 | Patient 4 | Patient 5 |
|---|---|---|---|---|---|
| Patient 1 | 1 | 0.87 | 0.7 | 0.17 | 0.71 |
| Patient 2 | 0.87 | 1 | 0.79 | 0.21 | 0.8 |
| Patient 3 | 0.7 | 0.79 | 1 | 0.23 | 0.9 |
| Patient 4 | 0.17 | 0.21 | 0.23 | 1 | 0.5 |
| Patient 5 | 0.71 | 0.8 | 0.9 | 0.5 | 1 |

|  | Gene A | Gene B | Gene C | Gene D | Gene E | Gene F |
|---|---|---|---|---|---|---|
| Patient 1 | 150 | 15 | 75 | 700 | 125 | 60 |
| Patient 2 | 120 | 30 | 5 | 100 | 80 | 70 |
| Patient 3 | 10 | 190 | 700 | 13 | 0 | 8 |
| Patient 4 | 20 | 130 | 800 | 4 | 105 | 90 |

FIG. 9

|  | Gene A | Gene B | Gene C | Gene D | Gene E | Gene F |
|---|---|---|---|---|---|---|
| Cutoff for over-expression | 80 | 60 | 500 | 83 | 50 | 14 |

FIG. 10

|  | Gene A | Gene B | Gene C | Gene D | Gene E | Gene F |
|---|---|---|---|---|---|---|
| Patient 1 | 1 | 0 | 0 | 1 | 1 | 1 |
| Patient 2 | 1 | 0 | 0 | 1 | 1 | 1 |
| Patient 3 | 0 | 1 | 1 | 0 | 0 | 0 |
| Patient 4 | 0 | 1 | 1 | 0 | 1 | 1 |

FIG. 11

|  | Gene A | Gene B | Gene C | Gene D | Gene E | Gene F |
|---|---|---|---|---|---|---|
| Factor A | 1 | 0 | 0 | 1 | 1 | 1 |
| Factor B | 0 | 1 | 1 | 0 | 0 | 0 |

FIG. 12

|  | Gene A | Gene B | Gene C | Gene D | Gene E | Gene F |
|---|---|---|---|---|---|---|
| Patient 1 | 1 | 0 | 0 | 1 | 1 | 1 |
| Patient 2 | 1 | 0 | 0 | 1 | 1 | 1 |
| Patient 3 | 0 | 1 | 1 | 0 | 0 | 0 |
| Patient 4 | 0 | 1 | 1 | 0 | 1 | 1 |

FIG. 13

|  | Factor A | Factor B |
|---|---|---|
| Patient 1 | 100% | 0% |
| Patient 2 | 100% | 0% |
| Patient 3 | 0% | 100% |
| Patient 4 | 33% | 67% |

FIG. 14

USER INTERFACE, SYSTEM, AND METHOD FOR COHORT ANALYSIS

This application claims the benefit of priority to U.S. provisional application 62/753,504, filed Oct. 31, 2018.

TECHNICAL FIELD

This disclosure relates to spatially projecting relationships in multidimensional data and, in particular, techniques for analyzing multidimensional datasets requiring the minimization of non-convex optimization functions.

BACKGROUND

Many fields of technology (e.g., bioinformatics, financial services, forensics, and academia) are scaling their information visualization services to meet consumer demands for identifying relationships between members of large sets of data that require substantial computational resources to perform with conventional techniques. As the scale of these datasets extend beyond tens of thousands of members, there is a need for an efficient and parallelizable technique to process, quantify, and display similarities (or dissimilarities) between members in an intuitive and understandable way. Existing techniques utilize clustering algorithms or multi-dimensional scaling algorithms which require minimization of an optimization function; which, for convex functions over large data sets, is relatively quick. However, when minimizing a non-convex function over a large data set, the requirement for computational resources, such as computation time, increases exponentially because optimization techniques cannot assume that any local minima detected is the global minima of the optimization function and must continue iteratively processing until all domain values of the function have been processed before concluding the global minima has been found. These techniques may consume significant resources and bog down processing and memory availability of the computing system that generates an ultimate user interface.

Such processing problems may be exacerbated when the user interface permits selection of a reference member from among the plurality of available members and/or customization of the criteria by which the members will be compared, and those abilities mean that the comparative determinations may need to be done "on-the-fly," as it would be impractical or consume too many system resources to pre-compile those calculations. For example, when comparing members in a multi-factor data set, convex optimization techniques (e.g. gradient descent) may be used to determine and visually quantify similarity among those members. Such conventional convex optimization techniques converge to a final value quickly, but they often result in an incorrect final value when the convergence is located at a local minima incorrectly presumed to be the global minima.

What is needed is a user interface and/or an underlying system and method that address one or more of these drawbacks.

BRIEF SUMMARY OF THE DISCLOSURE

In one aspect, a method includes the steps of receiving a first dataset, the first dataset having at least a first, second, and third member, where the first, second, and third members are matched to a plurality of identifiers, receiving a second dataset, the second dataset having a plurality of importance signifiers, where one more more of the plurality of importance signifiers are matched to one or more of the plurality of identifiers of the first dataset, generating a third dataset based at least in part from the first and second dataset, the third dataset having the plurality of identifiers of the first dataset matched with a plurality of scaled importance factors, and generating, by a processing device, a fourth dataset based at least in part on the first, second, and third datasets, the fourth dataset having a measure of similarity between the first member and the second member, a measure of similarity between the first member and the third member, and a measure of similarity between the second member and the third member. The method also may include the steps of receiving a selection of the first member from a user, identifying a first angular assignment for the second member and a second angular assignment for the third member, wherein the first and second angular assignments minimize a sum of squared error function and the second angular assignment indicates a similarity between the second member and the third member, and displaying, via a display operatively connected to the processing device, the first member at a focal point of the graphical user interface on the display, the second member at a first radial distance based on the measure of similarity between the first and second member and the first angular assignment, and the third member at a second radial distance based on the measure of similarity between the first and third member and the second angular assignment.

In another aspect, a system may include a display and a processor, the processor operatively connected to the display. The processor may be configured to receive a distance matrix for a plurality of patients and a patient of interest, assign a radial distance value between the patient of interest and the other patients based on the distance matrix value for each patient of the plurality of patients, generate an angular distance value for each patient and each other patient of the plurality of patients based at least in part on a measure of similarity between each patient, and minimize a cost function based at least in part on the angular distance value between each patient and each other patient of the plurality of patients. Minimizing the cost function may include calculating a patient contribution to the cost function for a plurality of angular distance values and selecting the angular distance value with the smallest patient contribution. The processor also may be configured to generate a radar plot based at least in part on the assigned radial distance value and generated angular distance value of each patient, and to cause the display to display the radar plot.

In another aspect, a method includes the steps of receiving a first dataset, the first dataset having at least a first, second, and third member, where the first, second, and third members are matched to respective gene expression counts, normalizing the respective gene expression counts relative to threshold values for each gene, selecting one or more member-comparison factors, identifying one or more meta-genes relevant to the one or more member-comparison factors, comparing normalized gene expression counts for the one or more meta-genes for the first member against normalized gene expression counts for the one or more meta-genes for the second and third members to generate a second dataset representing each member's relative overexpression relative to each meta-gene, receiving a selection of the first member from a user, identifying a first angular assignment for the second member and a second angular assignment for the third member, and displaying, via a display operatively connected to the processing device, the first member at a focal point of a graphical user interface on a display, the second member at a first radial distance based on the measure of similarity between the first and second member and the first angular assignment, and the third member at a second radial distance based on the measure of similarity between the first and third member and the second angular assignment.

BRIEF DESCRIPTION OF THE FIGURES

FIG. 9 is a matrix of exemplary gene expression counts for a plurality of cancer patients;

FIG. 10 is a matrix of exemplary gene counts taken from non-cancer tissues;

FIG. 11 is a matrix of the gene expression counts of FIG. 9, normalized using the gene counts of FIG. 10 as threshold values;

FIG. 12 is a matrix of exemplary latent over-expression factors;

FIG. 13 is a matrix reflecting an application of the factors of FIG. 12 to the over-expression states of FIG. 11; and FIG. 14 is an exemplary patient factor matrix representing each patient's relative over-expression relative to each factor.

DETAILED DESCRIPTION

Embodiments are described for identifying similarities between members of a data set and displaying these similarities in an intuitive and understandable way. A member of a dataset may be a person (e.g., a patient in a medical database or a customer in a financial database). In the instance that the member of a data set is a person, their personally identifiable information (e.g., social security number, address, or telephone number) and/or protected health information (e.g., health insurance provider/identification number and other identifying features) may be expunged to render the member unidentifiable. Alternatively, a member of a dataset may be an object (e.g., a tumor, a drug, evidence found in a crime scene, or a lunar rock specimen). Due to the vast nature of potential members of a data set, it is understood that the datasets may incorporate vastly different identifiers, features, or points of interest (e.g., physical characteristics of a person or object, genetic sequencing of a person or tumor, demographic information of a person or object, purchasing habits, frequency or dates of purchases) relating to the member and used to determine similarities between members of the data set. Similarities between members may include geographic proximity, shared genetic mutations, shared demographics or physical traits, shared chemical compositions, or shared molecular structures. Similarities may also be divergent in nature (e.g., neither member has a particular genetic mutation).

In one aspect, a comparative display may be presented to a user in order to compare a particular member of a dataset with other members of the dataset which share similarities. One such comparative display may display the particular member with an indicator such as a dot in the center of the display, and display other members with similar or distinct indicators such as additional dots around the center indicator. Such a comparative display is known herein as a "radar plot" or a "similarity plot." A radar, or similarity, plot provides two measurements for which to draw similarities: a radial distance for similarities between the center point and each plotted point and an angular distance for similarities between each plotted point.

Figure 1:
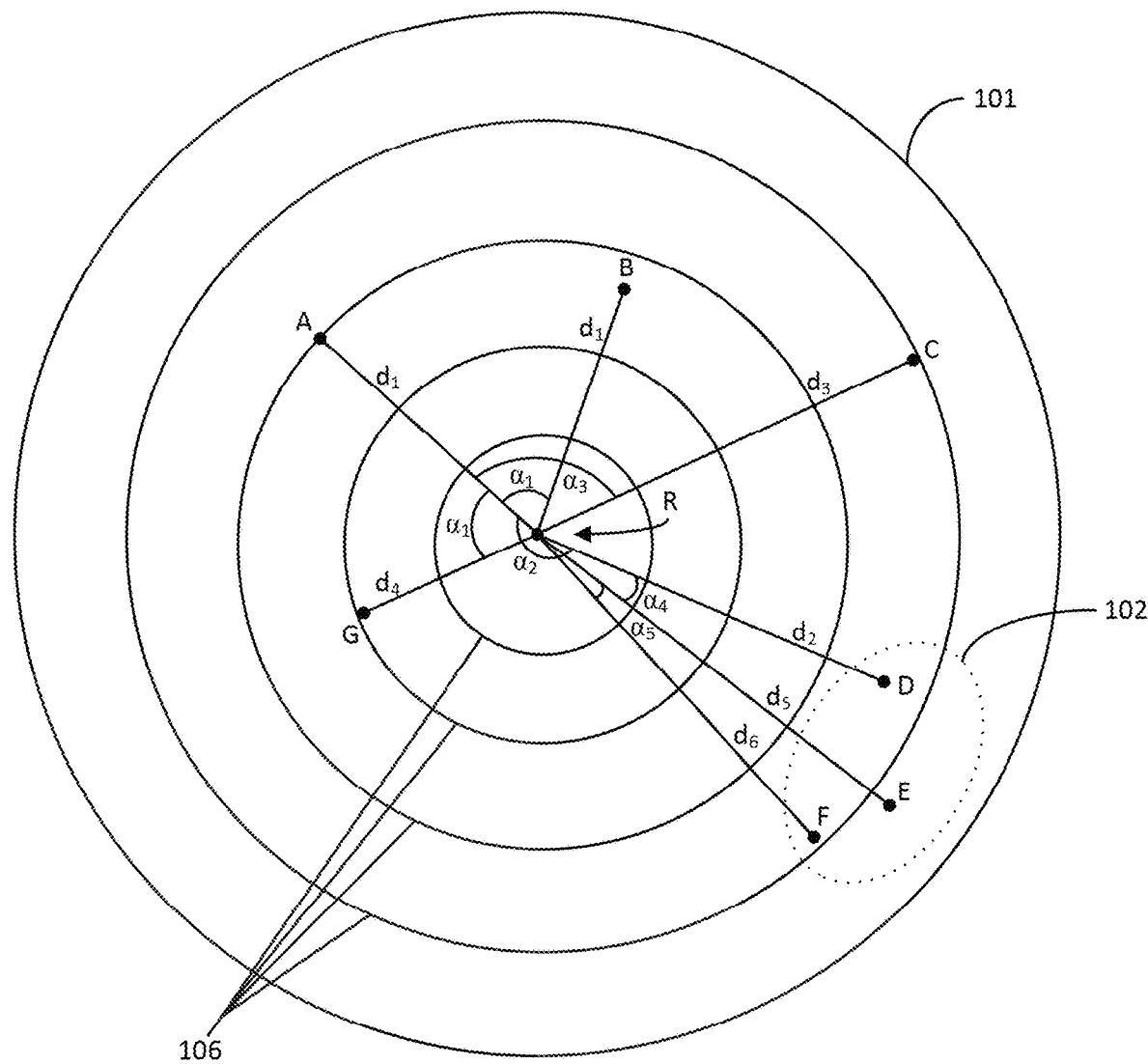
FIG. 1 is an exemplary image of a polar coordinate, similarity plot.

FIG. 1 shows a display of an exemplary similarity plot for a sample member cohort of members A, B, C, E, F, and G as well as reference member R. Reference member R is positioned in the middle of the similarity plot 101. Member sub-cohort 102 is also mapped on the similarity plot 101. In the display of FIG. 1, the distance from any indicator to reference member R reflects a similarity between the member represented by that indicator and reference member R, and rings 106 may be displayed concentrically around reference member R in order to help a user more specifically determine which of two members is closer to reference member R. Conversely, the angular distance between members other than reference member R reflects a similarity between those non-reference members, regardless of how similar those non-reference members are to reference member R. Members in FIG. 1 could be people, patients, objects, etc. as referenced above. Although the disclosure below at times refers to "patients" with reference to the figures, it should be understood that this is a general reference to "members" and that other members could be utilized as well.

In FIG. 1, members A-C and G are positioned at varying angular displacements to each other. Members A and B are the same distance ($d_1$) from reference member R, and member G is closest to reference member R, which indicates to the user that members A and B are both equally similar to reference member R as compared to the other members plotted on similarity plot 101, while member G is even more similar to reference member R than either of members A and B. Similarly, member C is the furthest point of members A-C and G from reference member R, which indicates that member C is the least similar member of members A-C and G to reference member R. Members B and G share the same angular distance $\alpha_1$ from member A, but in opposite angular displacements from each other. Thus, members B and G are equally similar to member A, but are dissimilar from each other. Such a dissimilarity may arise when members B and G share some similarities (which are also shared with member A) but have at least one stark contrast with each other (e.g., member B has a feature which member G does not).

Within the display, it may be possible to arrange a plurality of members in a common region (e.g., a sub-cohort), reflecting a determination that those members have sufficient similarities to one another to warrant such a grouping. For example, members D-F are in member sub-cohort 102. Their position close to one another on similarity plot 101 indicates that members D-F are much more similar to one another than to any of members A-C and G. While members D-F are clustered in member sub-cohort 102, member D is the most similar member to reference member R of the sub-cohort and member E is the least similar to member to reference member R. Member A and member E are angularly displaced from each other by 180 degrees. Their placement on opposite sides of reference member R indicate that they have zero similarity to each other (beyond similarities shared by every member of the cohort).

In the example of FIG. 1, the member of interest (R) may be placed in the middle of a polar coordinate system. The other members in the cohort are placed in consideration of: (1) their similarity or dissimilarity to the center member, which can be captured by radial distance ($d_i$); and (2) their (dis)similarity to each other, which can be captured by angular distance ($\square_i$). Member (dis)similarity to each other is represented in a range [0,180] degrees, so that when the angular distance is 0, the members have complete similarity, and when the angular distance is 180 degrees, the members have zero similarity based on the similarity features graphed (as discussed in greater detail below). For example, if members are patients being compared with respect to two features (e.g., presence of genetic mutations A and B), and one patient has mutated gene A but not mutated gene B while another patient has mutated gene B but not mutated gene A, these exemplary patients would have an angular difference of 180 degrees between each other (if the similarity plot was only showing similarities based on the presence of genetic mutations A and B).

In another aspect, the exemplary similarity plot of FIG. 1 may be updated by the user to filter out members having identified characteristics. For example, a member class comprising patients may be filtered by patients who have exhibited symptoms for a prolonged period of time, or patients who live in communities with known exposure to certain pathogens. Another member class comprising oncology patients may be filtered by patients of a specific diagnosis or patients who carry a particular genetic marker or genetic mutation. A member class comprising web-based customers may be filtered by customers whose first purchase corresponded with a promotional period or who have visited the website multiple times in a period of time without making purchases. In each case, the user may interact with the similarity plot by selecting from predetermined features to include or exclude members who have or do not have the features from the resulting plot. The user may also interact with the similarity plot by selecting a member. An interface (not shown) may be displayed to the user identifying the characteristics of the member which placed the member near neighboring members in the similarity plot. The interface may also allow the user to toggle inclusion and exclusion on these identified features to emphasize these features or hide them from view for further similarity comparisons. Furthermore, the interface may also allow the user to shift primary focus of the reference member to the newly-selected member. The user may reset any filtering criterion or reference member changes and restore the original similarity plot through the interface.

In one aspect, a dataset may be represented by an N×N distance matrix where N is the number of members. Each pair of members represented by an element pair (i,j) may have a normalized value [0,1] providing the similarity of member i with member j at the intersection of row i with column j and column i with row j, where 0 indicates no similarities and 1 indicates complete similarity. As expected, each intersection where i=j will indicate perfect similarity as a member compared to itself will always result in complete similarity. Representative examples provided herein may feature small sets to limit repetition, although it will be appreciated that the exemplary systems and methods are scalable beyond tens of thousands of members.

Figure 2A:
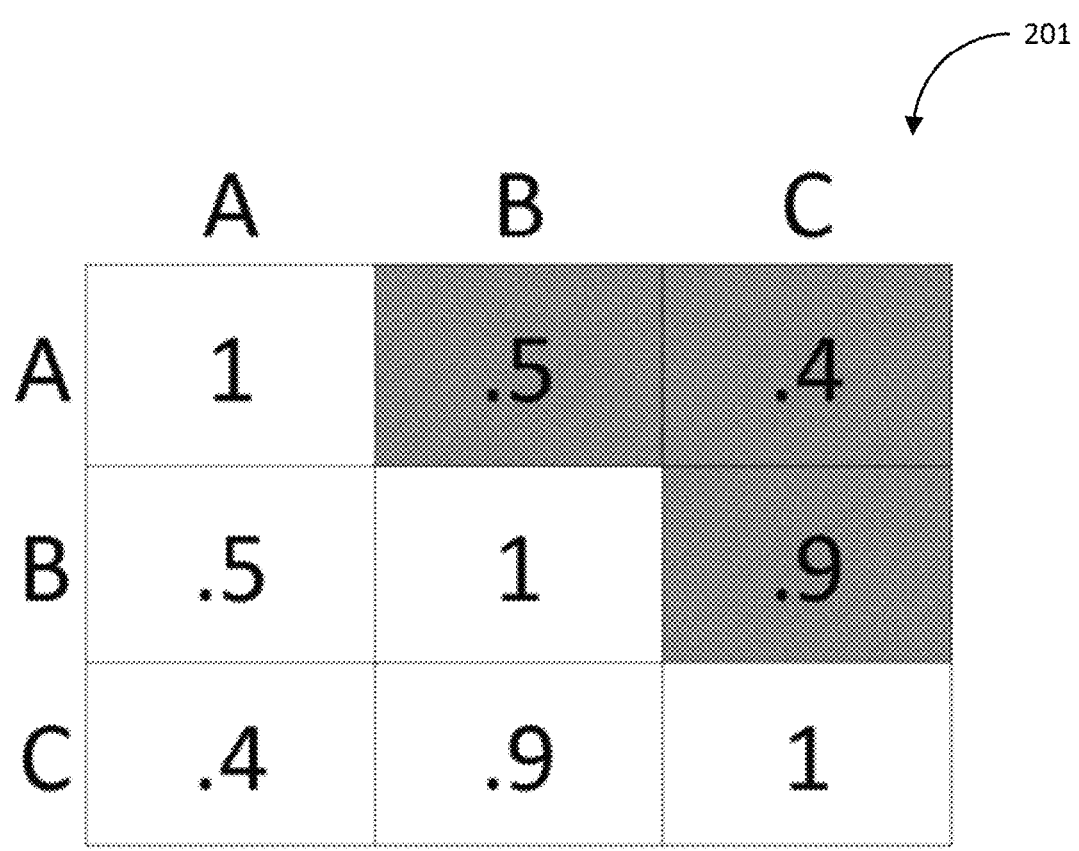
FIG. 2A is a comparison matrix with example normalized similarity values for comparing a plurality of members of a data set.

Turning now to FIG. 2A, an exemplary 3×3 distance matrix 201 with similarity measurements for three members (A,B,C) is depicted. In this representative embodiment, member A's similarity to member B is normalized to 0.5, member A's similarity to member C is normalized to 0.4, and member B's similarity to member C is normalized to 0.9. Similarity measurements that have not been normalized may be normalized according to any normalization algorithm. One such normalization algorithm is:

$$\text{Normalize(Value)}=(\text{Value}-\text{Min})/(\text{Max}-\text{Min});$$

where Value is the value of the dataset to normalize, Min is the smallest value in the dataset, and Max is the largest value in the dataset. The output of the normalize function is a value in the range [0,1]. The shaded region of FIG. 2A indicates duplicated distance values which do not need to be recomputed when a member is added into the distance matrix. The number of calculations necessary to populate a distance matrix is N(N-1)/2 as there are always N entries (the line of identity pairing each member with themselves) which are 1 and half of the remaining entries which are duplicates.

Figure 2B:
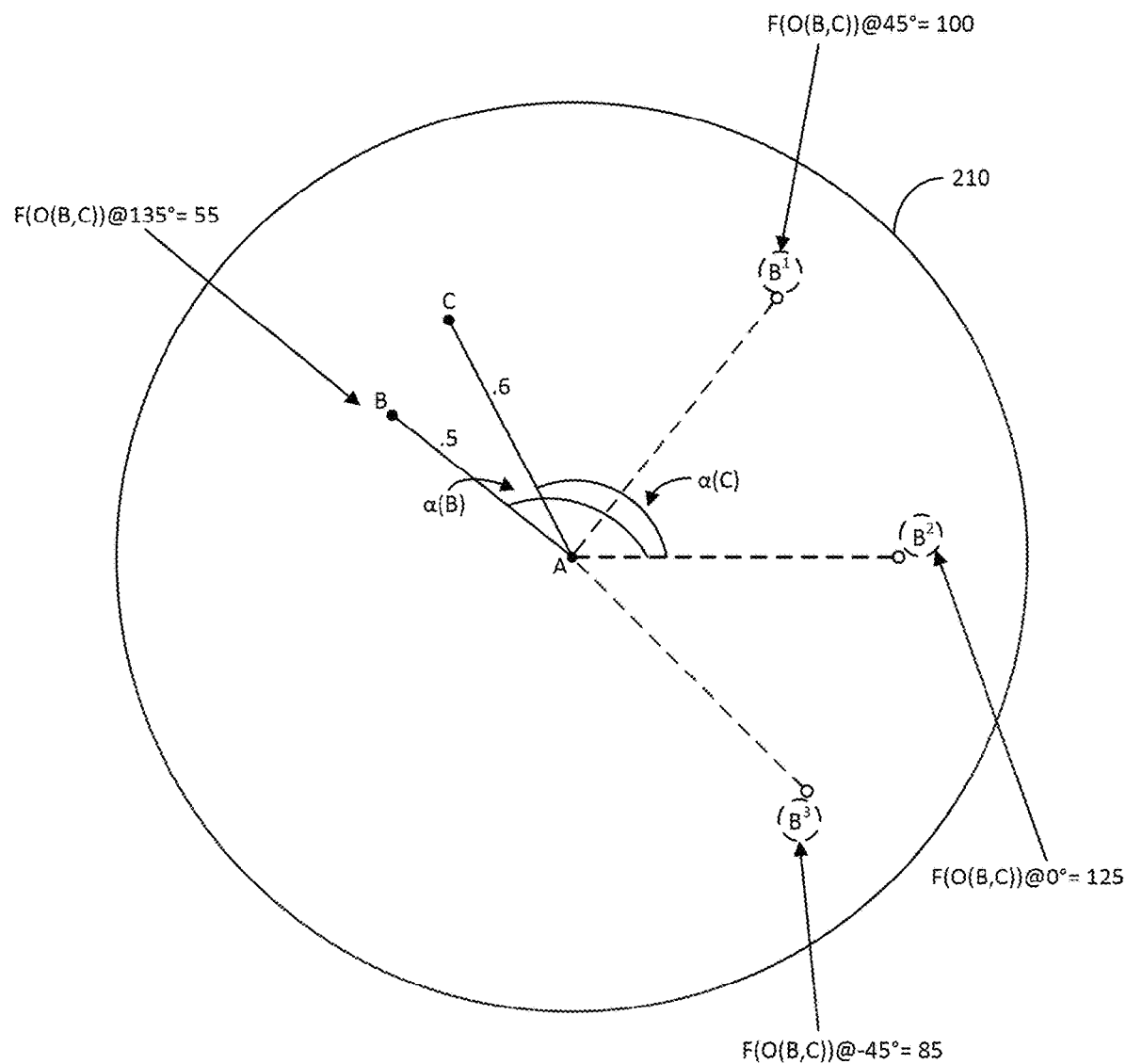
FIG. 2B is a second exemplary image of a similarity plot.

Turning now to FIG. 2B, similarity plot 210 is an exemplary plotting of members A-C of distance matrix 201 based on their similarities. In order to populate similarity plot 210, the radial and angular distances for members B and C must be calculated. For purposes of similarity plot 201, member A is the reference member or member of interest. The radial distance d(i,j) is calculated for each member with respect to member A by subtracting the element (i,j) corresponding to the similarity of member A of each member from 1. Thus, member B is plotted with a d(a,b)=1 −0.5=0.5 and member C will be plotted with a d(a,c)=1−0.4=0.6.

Selecting the order for plotting may be useful to minimize the number of iterations necessary to converge to an optimal similarity plot and thereby consume fewer system resources when performing the analysis, Methodologies for selecting a best order to plot members (e.g., highest average dissimilarity, lowest distance from average dissimilarity to 0.5) focus on placing the most distinct members around the similarity plot first to ensure accurate distribution with the fewest number of iterations. For example, under the highest average dissimilarity, the order of plotting may be chosen as follows: C: ((1−0.9)+(1−0.4))/2=0.35; B: ((1−0.5)+(1−0.9))/2=0.30; therefore, Member C, having the highest average dissimilarity (0.35) will be plotted before Member B having the next highest average dissimilarity (0.3).

In another example, under the lowest distance from average dissimilarity to 0.5, the order of plotting is chose as follows: C: 0.5-0.35=0.15; B: 0.5−0.30=0.20; therefore, Member C, having the lowest distance between its average dissimilarity and 0.5 (0.15) will be plotted before Member B, having the next lowest distance between its average dissimilarity and 0.5 (0.20).

The first member plotted may be placed at a random angular displacement, at zero degrees, or at any predetermined position. In similarity plot 210, member C is placed at 95 degrees. Member B is then plotted at an initial angle, which may be selected at random, selected from an array of angles, or placed at an angle corresponding to the degree of similarity identified in the distance matrix (e.g., smaller angles for high degree of similarity). Angular distances for each, −45, 0, 45, and 135 are shown on similarity plot 210. An optimization algorithm (discussed in more detail with respect to FIG. 3 below), F(O(B,C)), is calculated for each angle, and the angle which contributes the least F(O( )) is selected as the best fit. In this instance, member B is tested against angles −45, 0, and 45 degrees at $B^1$, $B^2$, and $B^3$ and then placed as B at angle 135 degrees, as F(O(B,C)) is the smallest value at that location.

Post-processing may be performed on the resulting angular distances in batches, or after all angular distances have been identified. Post-processing may include alternating points in a batch (swapping the angular distances that were assigned between points in the batch) and minimizing the cost function again. The angular distance assignment may be performed in parallel to greatly reduce processing time required to process large datasets. Picking members to process in parallel may best be performed by selecting members which are most dissimilar from each other to process in each parallel branch. For example, rather than picking a subset of members which have a radial distance which are very similar, picking members which have greater variation of radial distances may reduce the amount of post-processing necessary to generate a similarity plot. By ensuring that each processor, thread, computer, and/or server has a diverse subset of dissimilar members, each parallel branch may generate reliable angular distances in order for post-processing to result in the least amount of corrections. Furthermore, by ensuring that members in each parallel branch are dissimilar, spurious optimization may be avoided where two members end up being swapped back and forth in angular distances based on new minimums from the optimization cost function.

In another aspect, initial angular distances may be calculated based off a clustering model, where members are placed according to which cluster they were designated. Additionally, for purposes of parallelization, members of each cluster may be processed together or spread out among each of the parallel processing branches to keep dissimilar groups processed together and minimize the iterations required to arrive at convergence. Further parallelization techniques are described below with respect to FIG. 3.

Figure 3:
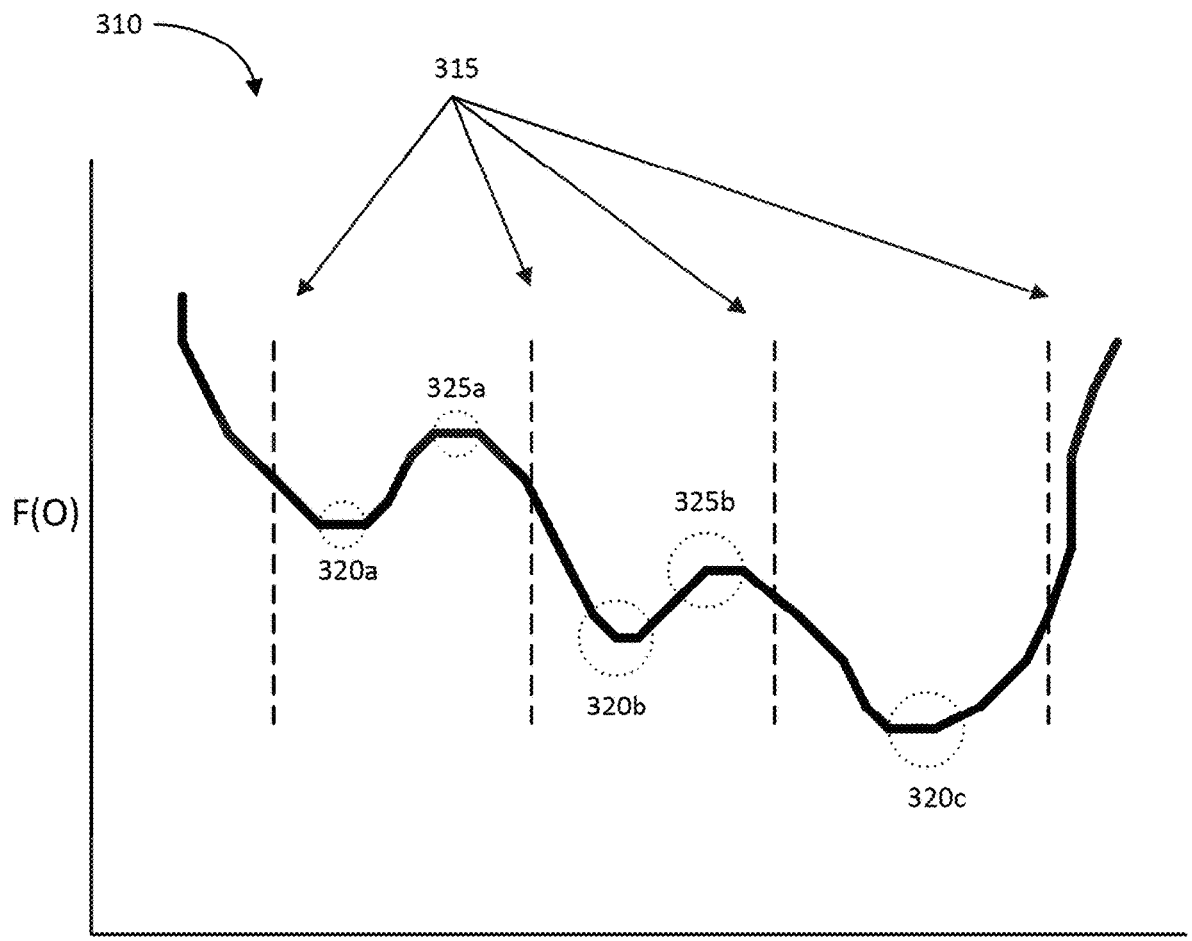
FIG. 3 is an example of a hypothetical non-convex graph applying a minimum sum of squared error optimization function.

Optimization algorithms for determining angular distances from a distance matrix may be non-convex in nature, implying that for every local minima that is identified in the normalization function, it cannot be determined that the local minima relates to the global minima identifying the best angular distance for each member plotted. In particular, FIG. 3 depicts one example of an available optimization algorithm (F(O)) and a graph of the minimization output.

As the number of data points, e.g., patients, being represented by indicators increases, it is a challenge to find a set of angles that does a good job of capturing dissimilarity over all pairs of patients, as, for "n" patients, there are n*(n-1)/2 distances to consider. Additionally, the computer processing resources required to analyze each pair of patients increases dramatically as the number of patients increases. In order to address these problems, the system may employ a model that utilizes one or more optimization methods. One approach is to minimize a sum of squared errors, which may be accomplished using a minimized sum of squared error (SSE) function. Other examples may include gradient descent and inverse quadratic interpolation methods. Utilizing a minimum SSE, the function will calculate, for all pairs of patients, the error between the known dissimilarity and an induced dissimilarity between the pairs of patients given their angle assignments. Additional details of this modeling, and of the data that may be used as inputs to the models are discussed in greater detail as follows.

In order to determine the relative positions of each indicator in the similarity plot relative to the reference patient indicator, an optimization method with a minimization of a cost function may be utilized to update positions over one or more cycles. In each cycle, each patient is temporarily positioned at a plurality of points defined by a shift vector. The point that results in a minimum calculated objective function becomes the patient's position in that cycle. At the end of a cycle, an overall objective function value is determined, based on the positions set for each patient. After each new cycle is computed, the resulting output of the overall objective function is compared to the result of the previous cycle to determine the rate of change between cycles. If the rate of change of the overall objective function value is below a predetermined threshold value, then the angular distances for each member have converged to the optimal placement within the similarity plot and the plot is finalized for display to a clinician or other user of the system. If the overall objective function value is not below the predetermined threshold value, then the angular distances of members are significantly changing and have not converged at the best visual representation of the member's similarities to one another, causing the method to initiate another cycle. Additional cycles are executed until the overall objective function value falls below the predetermined threshold value or the duration of executing the method exceeds a time limit.

As mentioned above, an algorithm may be employed that updates one patient at a time, e.g., by employing a "shift vector" to test the effect on an objective function of rotating a patient at each position within the shift vector.

One exemplary shift vector over a 360 degree rotational space is the vector v, which is made up of a set of shifts s. The set of possible moves is referred to as the shift vector as the position of the patient is moved clockwise or anticlockwise by a varying number of degrees. Each shift s is a numerical value. An exemplary vector v may be (−170, −160, −150, −140, −130, −120, −110, −100, −90, −80, −70, −60, −50, −45, −40, −35, −30, −25, −20, −15, −10, −5, −4, −3, −2, −1, 0, 1, 2, 3, 4, 5, 10, 15, 20, 25, 30, 35, 40, 45, 50, 60, 70, 80, 90, 100, 110, 120, 130, 140, 150, 160, 170, 180). When using shift vector v, each patient position p is "tested" at each shift s in the shift vector v. Use of a shift vector can remove the problems presented by multiple local minima.

It is possible that the number of shifts s in a shift vector can either be too small, so as to not produce sufficient granularity, or too large, so as to require an unacceptably large amount of computation and/or resulting processing resources. For example, a shift vector with 1 degree variation between shifts restricts a patient to being able to take one of 360 possible positions on the circle. This vector may provide significant granularity and an increased number of placement options, but it may do so at the expense of requiring substantial processing resources, particularly when it is considered that the number of shifts must be multiplied by the number of patients in the data set. Conversely, a shift vector comprising only four shifts s, e.g., (−90, 0, 90, 180) may consume substantially fewer processing resources, but it may do so at the expense of particularity and immediate user recognition, as it only allows for a data point to occupy one of four positions on the circle. Thus, for the choice of starting values and the start up process, there may be a trade-off between robustness and speed, In still another example, one way to be quick is to start all patients at the zero angle position and move patients in the order from the highest average dissimilarity patient to the lowest.

To increase robustness, it is possible to progressively increase the number of distinct points on the circle that the patient can take. For examples, a starting number of points at 0, 90, 180, and 270 degrees would put all the patients into a high level of 4 clusters. Progressively increasing the number of clusters up to the current max of 360 may increase the robustness of the output.

The algorithms described herein can be parallelized, whereby each patient is updated once in each loop across patients. Each patient can be updated simultaneously given the most up-to-date positions of other patients (some of which might be moved as the patients to whom they are being compared). In certain circumstances, parallelization can destabilize the robustness of the algorithm. On the other hand, robustness may be increased if used in conjunction with the approach of starting (outlined above) of increasing the number of clusters from an initial value, such as 4, up to a final value, such as 360.

It is possible in the fitting of the algorithm that certain sectors of the circle (i.e., ranges between certain angle positions) can be unstable. It is possible that within a range, the order is known but it is less clear from the data whether the order should be arranged in a manner that provides a clockwise or anti-clockwise plot. Thus, it may be prudent to run a check after a fit to know if there are such sectors. If so, flipping the angular positions of the patients from being clockwise to anti-clockwise (while maintaining the order within the range) may be useful to check if moving many points at a time can result in a reduction in the objective value.

The optimizations discussed herein reduce a non-convex function to a function that is solvable, quickly and with accuracy. Traditionally, a non-convex function lies in a domain (−∞, ∞). However, by mapping patients into a similarity plot and generating the optimizations around the angular distance of a circle, the system reduces the effective domain of the problem to one of range [0,360). In essence, the minimum position across the set of options does not require any assumption about the convexity of the function once reduced to a circle on an angular basis. This way, the algorithm is robust in case of moving a patient that could reasonably be placed on either side of the circle—the algorithm will always choose the considered angular position that corresponds to minimizing the overall objective function.

The new approach compensates for the non-convexity induced by mapping to the circle by using the fact that the circle is a limited space to map to. Given that the circle is a constrained space, it is possible to explore the space well by looking at a number of discrete points and choosing the best place to move to without any need to assume convexity to be able to make that choice.

The overall objective function is the sum of a fit function for all pairs of patients. In one instance, the fit function for a pair of patients i and j (where patient i is not j) looks at the square of the error between the dissimilarity between the two patients and the approximation of the dissimilarity from their angular positions. The dissimilarity between patients may be scaled to have a minimum value of zero and maximum value of one. The approximation of the dissimilarity between patients from their angular positions is the absolute difference between their angular positions (in degrees) divided by the maximum value of 180 degrees, such that the approximation will have a minimum value of zero and maximum value of one.

In one example, the objective function may be defined as:

$$\text{Objective} = \sum_{i=1}^{i=n} \sum_{j=1}^{j=i-1} (d_{i,j} - e_{i,j})^2$$

where $$e_{i,j} = \frac{f(A_i, A_j)^2}{180}$$

In this equation $d_{i,j}$ is the dissimilarity between patient i and patient j; $e_{i,j}$ is the approximation of the dissimilarity between patient i and patient j due to the angular positions; $A_i$ is angular position of patient i (in degrees) and $A_j$ is the angular position of patient j (in degrees). The function f, returns to the absolute value of the minimum distance in degrees that one patient i needs to be rotated to move to the other patient j (for example, if two patients were at 90 and 100 degrees, f would return 10 degrees; if two patients were at 350 and 10 degrees, f would return 20 degrees).

The algorithm may iteratively update one patient at a time, over one or more cycles. Specifically it may iterate over many cycles, where in each cycle it updates the position of each patient one at a time. The algorithm may iterate over cycles of updating patients positions until the change to the overall objective function over an entire loop is less than some (relatively small) value.

Turning to FIG. 3, an exemplary depiction of minimum SSE is shown in plot 310. For each new member added to a similarity plot, the SSE is calculated across all angular distances. As each patient added represents the Nth patient, then only N-1 calculations must be performed between the newest patient and the N-1 patients. This presents a unique consideration for parallelization as for each new patient N, given that the previous N-1 patients were picked for plotting based on their dissimilarities or according to their distributed clusters, a presumption can be made that for each additional patient, each other additional patient does not require precise knowledge of the patients being placed on the plot in parallel. For example, after plotting the first 100 patients, according to their dissimilarities so that they are distributed across the similarity plot fairly evenly, adding additional patients may serve to only define clusters of patients rather than establish a new cluster which must be accounted for by relocating many patients. Therefore, parallelization may be accomplished by adding a group of patients at a time, using only the currently plotted patients, and allowing the natural iterative nature of the minimization of the optimization function to finely tune the bulk additions in the remaining cycles. Under this process, the resulting SSE is stored for each new angular distance, and the angular distance contributing the least SSE is assigned to the corresponding member.

In another aspect, angular distances may be calculated utilizing a sliding window. For example windows 315 identify a first, second, and third subsection of plot 310 to evaluate the SSE for any local minima. Calculating the SSE over the first window may identify local minima at 320a, or a change from positive to negative SSE change at point 325a to identify that the function is a non-convex function with multiple local minima. As the sliding window 315 shifts, local minima 320b may be identified and added as the current minimum SSE for element i,j. Another local maximum may be identified signifying yet another possible local minima. The sliding window 315 then may shift to the final window and identify local minima 320c. As the entire domain of available angles has been checked, local minima 320c is identified as the global minima for the SSE for element i,j and the corresponding angular distance will be set for the current member. While not shown, it is possible for each window 315 to have zero local minima or more than one local minima.

Other optimization functions may be considered having different cost functions to minimize. For example, other optimization functions may include: 1) a sum of absolute (rather than squared) distances, 2) setting a maximum for the possible squared differences (i.e., the value for a pair of patients is the minimum of □ and the squared difference, where □ represents the angular distance between two patients, as seen in FIG. 1), 3) rather than squaring the difference, change the power to a set value, e.g., $\gamma$, where all absolute differences are raised to the power of $\gamma$), or 4) using an auxiliary function, such as:

$$f(distance_{i,j}) = \sin\left(distance_{i,j} * \pi - \frac{\pi}{2}\right)^{0.5} + 0.5$$

As is well appreciated by persons of ordinary skill in the art, the listing of optimization and cost functions is merely illustrative, as different functions may be picked for different datasets to reduce processing time or computation resource demand.

Figure 4A:
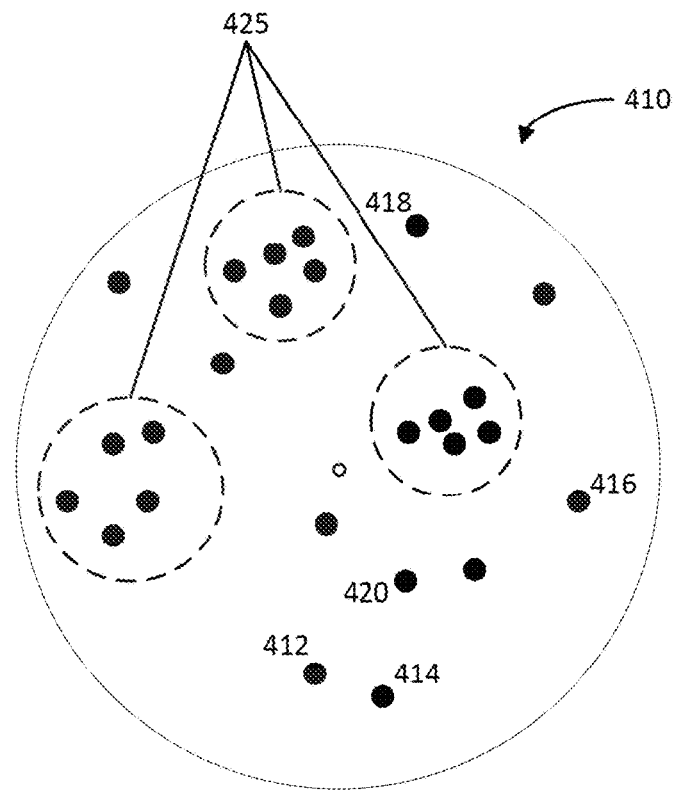
FIG. 4A is an example of an image incorporated into a user interface for visually examining similarity within a patient cohort.
Figure 4B:
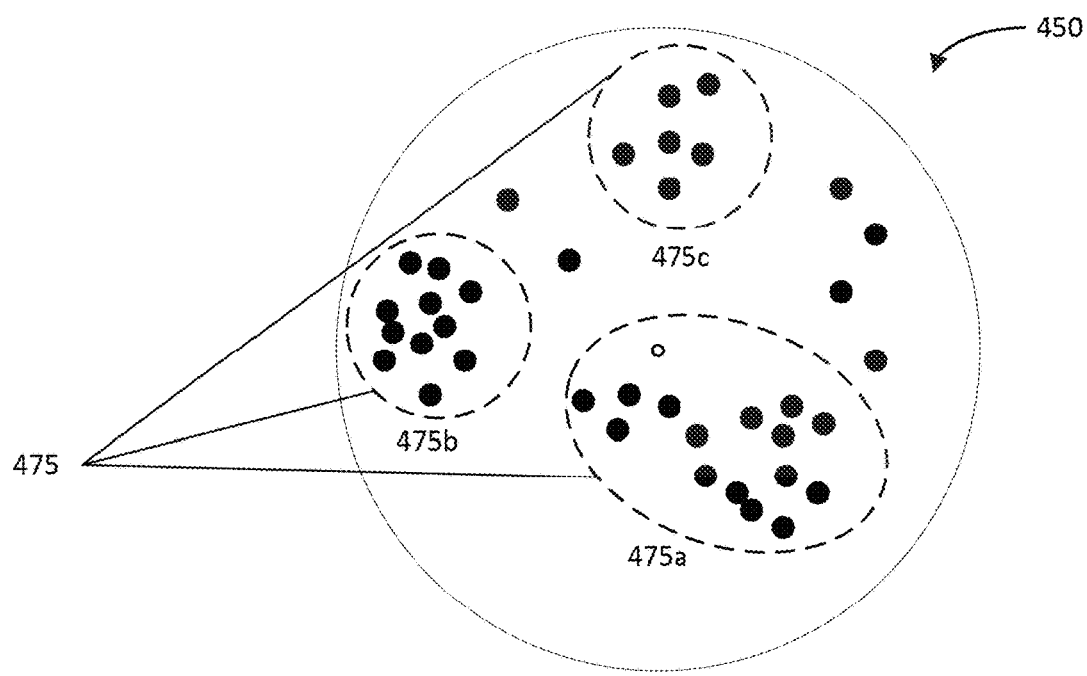
FIG. 4B is an examine of an image incorporated into a user interface for visually examining similarity within a finance cohort.

Turning now to FIGS. 4A and 4B, additional views of similarity plots in which considerably more members are represented by indicators as compared to FIG. 1 are shown. In order to compare a plurality of different patients based on one or more system- and/or user-defined criteria, the system may establish some form of "similarity metric" that can quantify a degree to which the patients are similar. In this image, an exemplary member classification may include a patient cohort for a physician. Within that context, the overall aim of the similarity metric may be to be a good summary of the information that is learned from the patient files, including clinical data, patient demographic, and even test results such as genetic sequencing, magnetic resonance imaging, or x-rays. The similarity metric may balance a user's prior expectations with an ability to discover new aspects that were not already known. Additionally, a key aspect of a patient similarity metric may be the ability to learn or accept varying weights for different genes, as certain genes may be more important than others, depending on the analysis ultimately being done. The metric preferably should accomplish two things: accurately guiding users to better clinical decisions, and maintaining consistency with what a user would expect to be there.

As with the interface of FIG. 1, each dot in FIGS. 4A and 4B may represent a distinct patient. Also as with the interface of FIG. 1, the patients represented by indicators 412 and 414 are more medically similar to one another than are the patients represented by indicators 416 and 418, as signified by the angular distance between indicators 412 and 414 being smaller than the angular distance between indicators 416 and 418. Conversely, the patient represented by indicator 420 is more medically similar to the reference patient at the center of the plot, as signified by the radial distance between the reference patient and that indicator 420 being smaller than the radial distances from the reference patient to any other member.

In both interfaces, the patient could be a patient of the clinician viewing the similarity plot, a patient of another clinician within the same organization, or a patient of another clinician in a different organization. Patients located in sub-cohorts 425 may possess similarities which are of great interest to the physician in determining an appropriate course of treatment. For example, if patients in sub-cohorts 425 respond well to treatments that each target a genetic mutation shared by the reference patient and each respective sub-cohort, a physician may consider discussing each treatment option with the reference patient. Alternatively, if patients in a sub-cohort which is further away from the reference patient respond well to a treatment, but patients which are in a sub-cohort closer to the reference patient do not respond well to the treatment, a physician may decide to consider other treatments options for the reference patient.

FIG. 4B may represent a similarity plot 450 for a web-based company's customers over the last six months. Similarities considered in the distance matrix may include purchase amounts, purchase frequency, dates visited, frequency of visits without a purchase, customers who abandoned a purchase at a particular stage in the checkout process, or any other demographic information or customer information gathered by the web-based company or their affiliates. A reference customer may be a customer who has added an item to their online cart, but have not checked out. Sub-cohort 475a may include customers who are geographically close to the reference customer and who also have not checked out. The angular similarities may indicate that these customers have abandoned the check out processes after viewing the shipping charge to their geographical region. The company, upon noticing this similarity, may offer a discounted shipping coupon to members of cohort 475a. The user may observe that members of sub-cohort 475b completed purchases using a coupon code for 15% off one item in their order or that members of sub-cohort 475c have visited the site several times before making a purchase shortly after the shopping portal was restructured to be more user friendly. By observing the similarities and/or dissimilarities of customers in their similarity plot, the company may make decisions on how to best influence consumer purchasing habits that are not immediately obvious otherwise.

Still other uses for a user interface such as those shown in FIGS. 4A and 4B are possible. For example, another interface may be used to compare drug-to-drug cohorts, where similarities may be based on, e.g., one or more of molecular composition of drug, FDA approvals, successful clinical trials, targeting of specific illnesses, pathogens, cancers, or other factors.

As discussed above, when comparing two patients based on a plurality of factors that include genetic similarity, certain gene similarities may be more significant than others. The present metric may be configured such that key genes dominate that similarity metric (for example, sharing a PIK3CA mutation is important), irrelevant of varying levels of background mutations of low interest (for example, patient A could having 1 interesting mutation and 9 of low interest, where patient B could have 3 mutations of interest and 900 of low interest). By focusing on the dominant genetic variants or similarities, the system may implement a more useful process than a situation where a user simply filters patients based on the presence or absence of mutation in key genes to find a cohort of the right size.

Figure 5A:
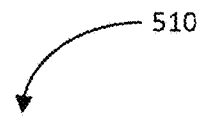
FIG. 5A is a table of exemplary mutation states for a plurality of genes for multiple patients.

Turning now to FIG. 5A, an example of mutation states for a plurality of genes for multiple patients is depicted. In this example, a value of 1 indicates a mutated gene for that patient and a value of 0 corresponds to a non-mutated gene. Given an exemplary DNA genetic mutation cohort 510, there may exist a series of sequencing results for each patient listing the genetic mutations present in the patient. Given sequencing results, every gene is given a status of mutated or not-mutated, where a mutated gene is a gene with at least one protein altering mutation. Specifically, the mutation may be exonic and non-synonymous. In addition, the system may be configured to incorporate quantitative information on how pathogenic a mutation is, e.g., by ascribing values to pathogenicity prediction, likelihood of protein termination, likelihood of aberrant protein, likelihood of changing key binding targets, etc.

Figure 5B:
FIG. 5B is a table of exemplary weights to apply to each of the genes identified in FIG. 5A, reflecting an appreciation that certain gene mutations are more significant than others when comparing patients.

It will be appreciated that simply having a mutated gene may not, by itself, represent anything significant, either by itself or in comparison with the genetic sequence of another patient. Thus, the DNA metric that values the mutations in each gene may vary differently by applying a weight between 0 and 1 for each gene. Exemplary weights 520 for each of the genes of 510 are shown in FIG. 5B.

In previous systems, gene importance scores were generated using the frequency of mutation as a proxy for the gene importance. In contrast, the present system may process the actionable gene database to explicitly generate an importance for each gene from the evidence for, and the impact of, a mutation for helping drug choice. Genes not in the actionable gene database have a weight of 0. Conversely, a gene of weight 1 has a highest confidence that it affects the action of an FDA-approved drug for the cancer type in question for that variant. Other factors for adjusting a gene weighting may include evidence of being a driver gene in the metric and an assessment of DNA variation at the variant level, rather than just at the gene level.

Weights may be determined based on evidence that a gene is useful in comparing patients in a cohort. For example, the presence of an approved treatment for a specific gene mutation may be used to modify a weighting. In particular, the existence of an FDA-approved drug for a mutation in a specific gene for a specific cancer type may result in the weighting for that gene being increased and/or set to "1." (Such weighting may be both gene specific and cancer-specific, as the same drug may not be approved for a mutation in the same gene for a different cancer type, which may result in no change to that gene's weighting in that circumstance.)

In another aspect, importance scores may not be known in advance. In those situations, exemplary models for generating a vector of importance scores may be generated by utilizing a machine learning model, training the model on patient data (e.g., demographics), clinical data (e.g., diagnosis and results), genetic data (e.g., genetic mutations exhibited in patient), and allowing the machine learning model to determine weights for each gene based on the output machine learning model.

Figure 5C:
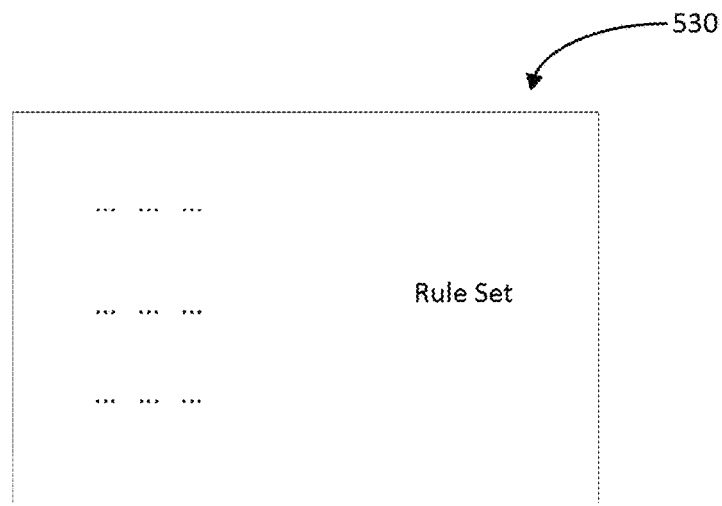
FIG. 5C is a depiction of an exemplary rule set, such as the rule set provided in FIG. 6, to be determine the gene weighting of FIG. 5B.
Figure 6:
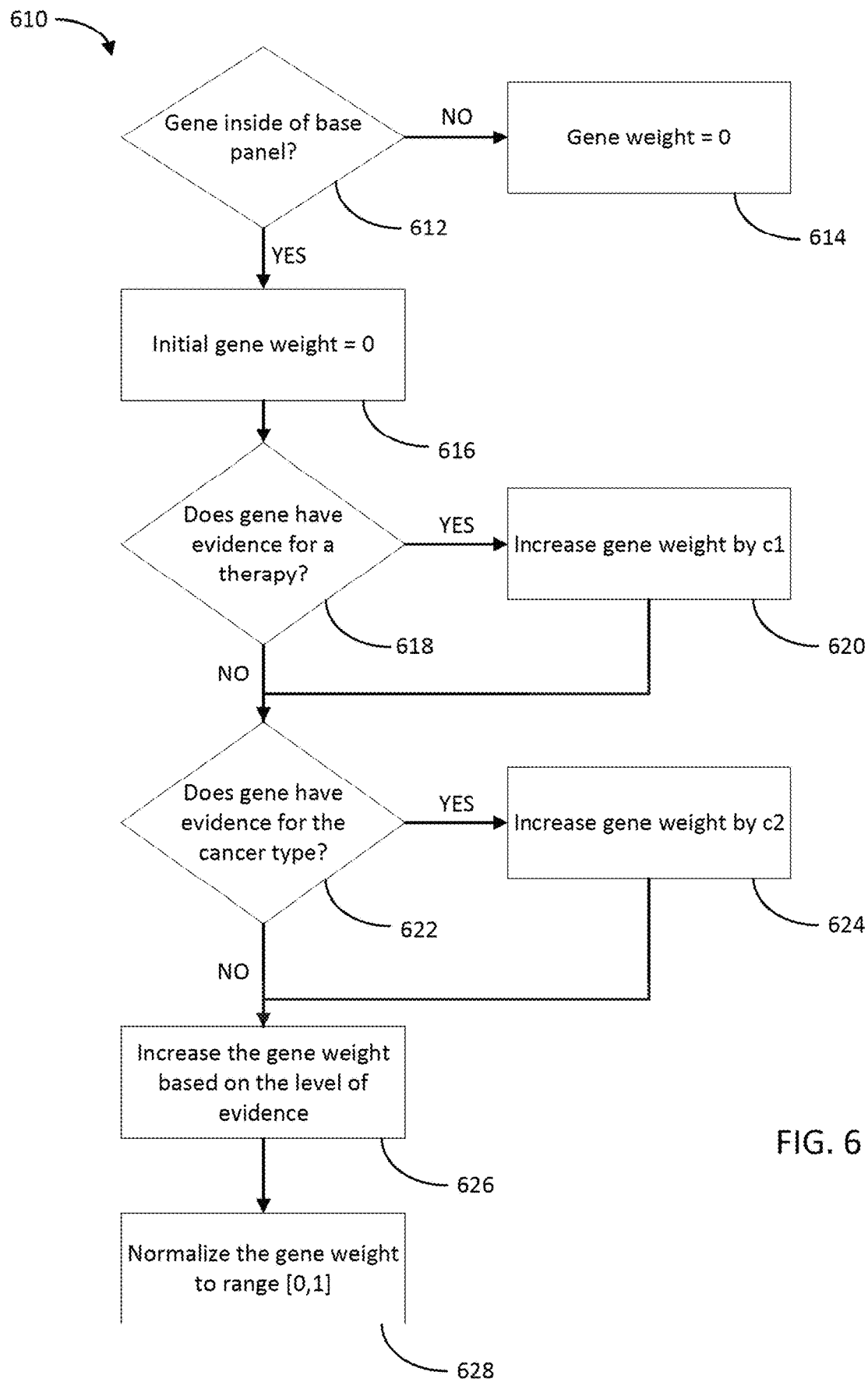
FIG. 6 is a flowchart depicting a rule set for determining weights for a plurality of gene mutations.
Figure 7:
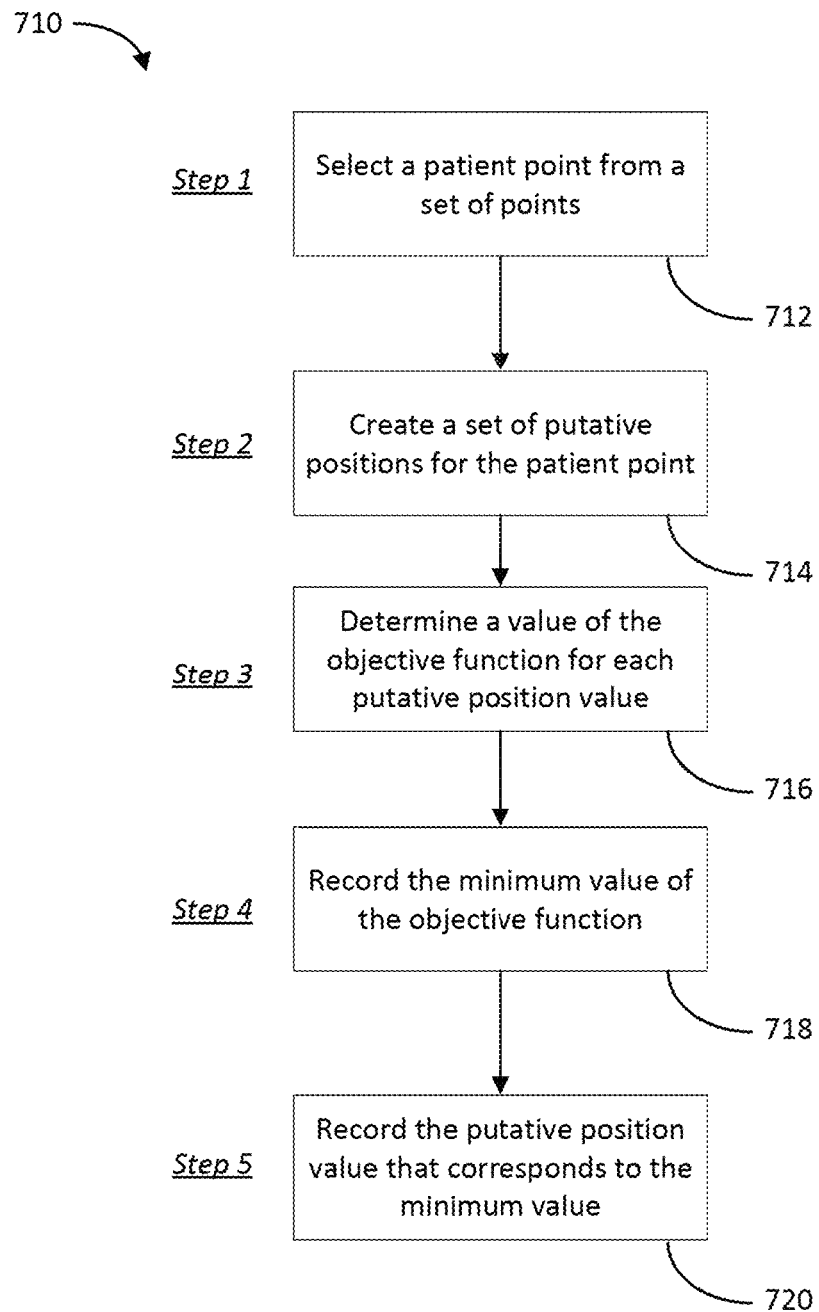
FIG. 7 is a flowchart depicting a rule set for determining angular distances between points in a similarity plot.

In still another aspect, importance scores may be calculated by following a rule set 530, as generally shown in FIG. 5C. For example, in one rule set as depicted in FIG. 6, a base weight of 0 is assigned to all genes. If a gene is not included in a genetic base panel at step 612, then the weight remains 0 at step 614 and the next gene's weight is calculated. If a gene is included in a genetic panel, information is extracted from the panel by starting with an initial gene base weight of 0 at step 616. Such information may include whether there is an FDA approved therapy targeting the genetic mutation, as at step 618. If such a therapy exists, the gene weight may be increased as at step 620 using metric c1, discussed below. If no such therapy exists, then there may be a determination as to whether the gene has an evidence for the cancer type being queried, as at step 622. As before, if such evidence exists, the gene weight may be increased as at step 624 using metric c2, discussed below. The gene weights then may be increased based on the total level of evidence at step 626 using a third metric c3. Finally, at step 628, the gene weight may be re-scaled using a maximum weight of one, e.g., after this procedure has been undertaken for each gene under consideration.

As discussed above, at step 620, weights may be increased using a metric c1. This metric relies on a level of evidence for the particular gene/therapy combination to increase the weight, where the gene residing low on a spectrum results in a low increase to the weight and residing high on the spectrum results in a high increase to the weight. In particular, there may exist levels of evidence for a therapy for a particular gene, e.g, 1 to 7, where 1 is the best and 7 is the least informative. Such levels may be determined based on one or more factors including, e.g., a number of patients that have undertaken the therapy with favorable results, a percentage of remission after 1 year, 2 years, 5 years, etc., a percentage reflecting an existence or lack of adverse side effects, etc. In another embodiment, the existence of evidence that a gene has a therapy which targets the gene greatly increases the gene's weight and a gene which has no targeted therapies does not increase the gene's weight.

Similarly, at step 624, weights may be increased using a metric c2. Like c1, this metric may rely on a level of evidence for the particular gene/cancer type combination to increase the weight, where the gene residing low on a spectrum results in a low increase to the weight and residing high on the spectrum results in a high increase to the weight. As with c1, there may exist different levels of evidence for the particular cancer type, where stronger correlations may be reflected in larger values of c2. In another embodiment, the existence of evidence that the gene is correlated with a cancer type, increases the gene's weight based on the level of correlation and a gene which has no correlation to a cancer type does not increase the gene's weight.

Other evidence may be weighed at step 626. Such evidence may include genes which do not have known, established correlations to certain cancers but where certain variants of the gene may hold a slight correlation. A varying level of c3 may be applied based on the strength of the correlation of each variant present.

Once the weights c1, c2, and c3 are determined at steps 620, 624, and 626, respectively, it is possible that the sum of the weights c1+c2+c3 for a gene may be greater than one. Thus, the step 628 normalizes the gene weights by dividing each specific c1+c2+c3 gene weight by the sum of the maximum values for each metric, i.e., c1_max+c2_max+c3_max.

In addition to analyzing patients for similarities or commonalities of at least one somatic mutation in common, the DNA metric also may account for when a pair of patients has no mutations in common in order to separate out patients that could nearly be close (if they had had a few key mutations) from patients that are definitely very different.

If two patients have no mutations in common, the metric for that pair may be 0. Conversely, in the event that a pair of patients has at least one mutation in common, the metric may be a sum of the gene importance scores across the mutated genes that they have in common, taking into account the gene weighting discussed above. The use of gene importance scores may lead to a focal point on the very important genes so that the genes that are of background importance are not that influential.

Regarding step 628 on FIG. 6, the sum of gene importance score scores may be rescaled by the geometric mean of similarity of the pair of patients to themselves. This means that the mutated genes that are not in common are taken into account. For example, a patient that shares one mutation with a reference patient could be deemed to be closer than a second patient with two shared mutations if the second patient has vastly more mutations that the reference patient does not have. In the event that a pair of patients has no mutations in common, the metric may be generated from the sum of the scores of the mutations in the first patient but not the second and the sum of the scores of the mutations in the second patient but not the first.

Applying the methodology described above, the overall metric may range from zero (zero similarity) to 1 (complete similarity). When the pair of patients have no mutations in common, the overall metric ranges from zero (zero similarity) to a quarter, and when the pair of patients have at least one mutation in common, the overall metric ranges from a quarter to 1 (complete similarity). A dissimilarity metric may be calculated by subtracting the similarity metric from 1. The dissimilarity metric is used in the objective function below.

One exception to this situation is the case where both patients have no mutations. In this case, the similarity may be defined to be 1. That case is always the 'closest' possible patient, given that there are no mutations in common, and they will overlap each other in any plot as they are perfectly similar.

Figure 5D:
FIG. 5D is a table representing an exemplary DNA comparison matrix for a plurality of patients.

Using the methodology, FIG. 5D provides an example of a DNA comparison metric for the pairs of patients 1-5 identified in FIG. 5A and using the cohort values 510 in FIG. 5A and the weights identified in FIG. 5B. It can be seen in this figure that patients 3 and 5 are the closest in similarity 540, even though patients 1 and 2 share more mutations. We can also see that patient 1 and 4 are the furthest away from each other as there are many key mutations that one patient has but not the other.

As discussed above, the system may take one or more additional factors into account in determining a similarity between a pair of patients, such as the presence of an FDA-approved treatment for a shared gene mutation. Other exemplary factors may include sequencing depth, frequency of somatic mutation, and variant level importance and pathogenicity.

Once similarities have been determined for each patient pair (where each pair includes a reference patient and one of the other patients stored in a database), the system may generate a user interface that includes a plot specific to the reference patient. In the plot, the system explicitly shows the similarity of the patients in the cohort to this reference patient and also indicate any clustering in the type of the patients that are similar to the reference patient (e.g. there might be 3 distinct types of similar patients). That plot may take the form of the similarity plots discussed above and shown, e.g., in FIGS. 1, 2, and 4A-B.

In particular, polar coordinates may be used to plot similarity to both the reference patient and the types of patient in the cohort. As discussed above, the distance from the center (i.e., the radius) indicates the similarity of the patient of interest (which is at the center) to the patients in the cohort, and the angular position approximates the similarity of the patients within the cohort to each other (similar types of patients can be seen at similar angular (or o'clock) positions, where the patients on the opposite side of the circle are the most dissimilar).

As described above with reference to FIGS. 2A and 2B, the present disclosure discloses a method of minimizing an objective function with respect to a particular patient point in a single cycle. With consideration of an unknown distance matrix but having a patient cohort database featuring at least patient DNA metrics including which genetic mutations are expressed by each patient, a similarity plot providing a visual comparison of the similarities of a physician's patients may be generated and displayed. Following the distance matrix calculations as described above with respect to FIGS. 5A-D, FIG. 7 describes an exemplary system which may compute radial and angular distances for each patient in method steps of 710. In step 1, 712, a patient point is selected from the set of patient points. The selection may be made on an ordered basis, randomly, according to patient clustering, or even to maximize the dissimilarity between the previous plotted patient(s) and the current patient. In step 2, 714, a set of putative positions are created for the patient point. One way to create the set of putative positions is to add the patient point to a shift vector, resulting in a set of putative position values equal to the shift vector values offset by the patient point position. These shift values may be expressed as varying intervals from 0 to 360 degrees of shift or any other known algorithm which optimizes placement accuracy or speed. In step 3, 716, each value of the objective function is determined for each value in the set of putative position values. In step 4, 718, the minimum value determined from all such determinations is recorded. In step 5, 720, the putative position value that resulted in the minimum objective function value is recorded in the patient point record. In other words, the patient point position is updated with the putative position value.

If any patient positions remain which have not been evaluated during the cycle, after each patient position has been evaluated by the method described above with regard to FIG. 2, the value of the overall objective function is determined and compared to a predetermined threshold value. The scale of this threshold would reasonably increase with the size of the cohort. An exemplary threshold value for a cohort of about 250 patients is about 0.5. The relationship between the threshold value may be linear to the size of the cohort. For example, the threshold may increase by 0.00002 per pair of patients. Determining the threshold is a matter of the degree of specificity to be displayed. For a small display, a high degree of specificity is not needed as a few degrees of variance are not visible to a user looking at the plot. However, for a similarity plot that is displayed in a sufficiently large display, a smaller threshold may be preferred, as a few degrees of variance may be much more noticeable on the similarity plot.

Because each patient's position is updated on its own, the overall objective function is being evaluated for that one position for that patient, and only the dissimilarity between the patient being updated and the other patients may be considered. As such, the system only may consider a patient specific objective function (with only n-1 dissimilarities) to update the patient's position, as all the other contributions to the overall objective function do not relate to that patient and, consequently, are constant. Minimizing the per-patient objective function to find the new position for that patient, thus, may be the same as minimizing the overall objective function. The advantage to minimizing the per-patient objective function for each patient one at a time, is a dramatic increase in the speed of the algorithm with no loss in accuracy. By minimizing the per-patient objective function it may be necessary only to consider n-1 patient pairs each time a patient is updated, rather than all n*(n-1)/2 patients pairs. Once all patients in the cohort have been plotted, the similarity plot may be displayed to the physician.

Figure 8:
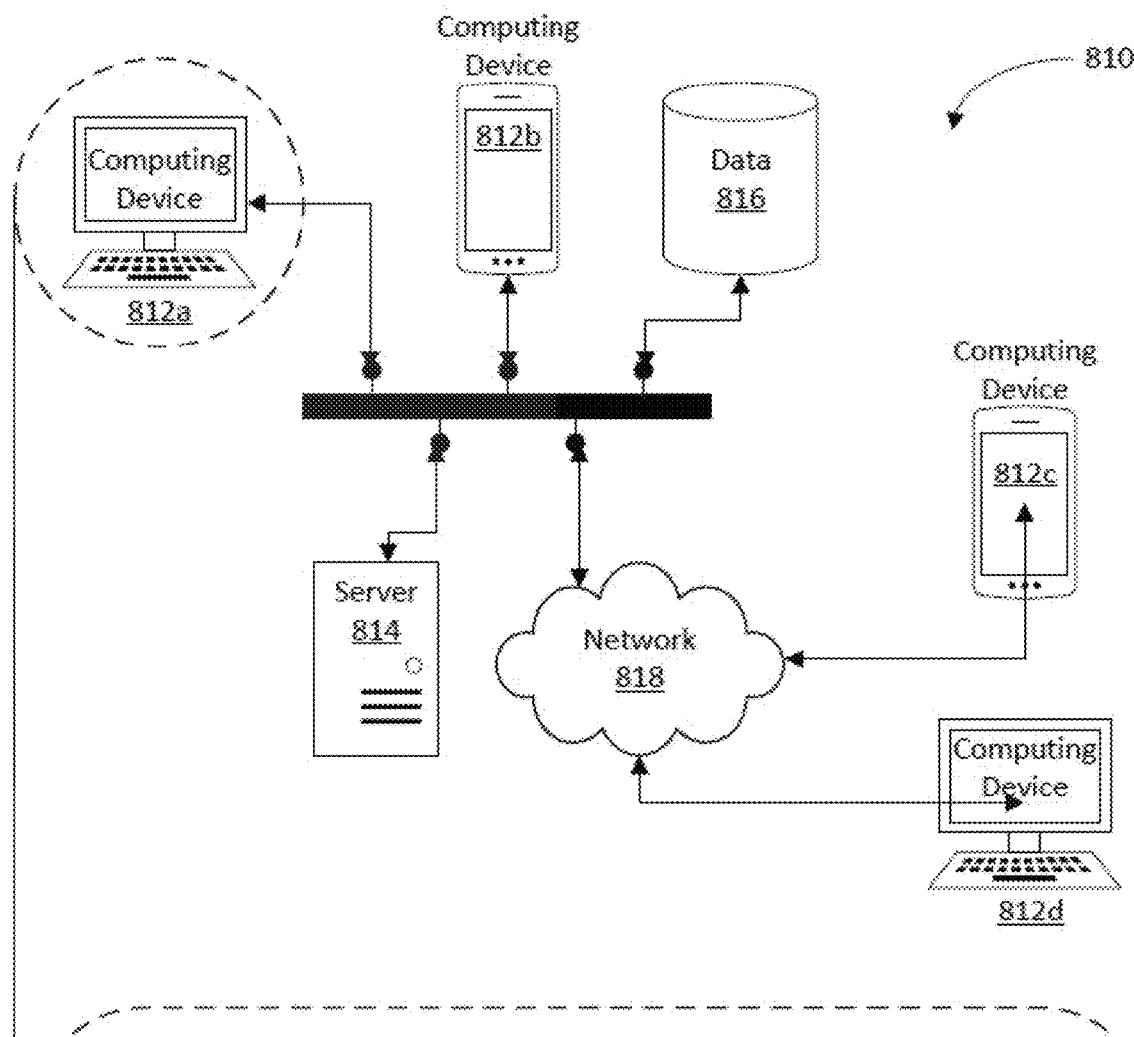
FIG. 8 is an exemplary diagram of a system for carrying out the method and generating the user interfaces described herein.
Figure 8:
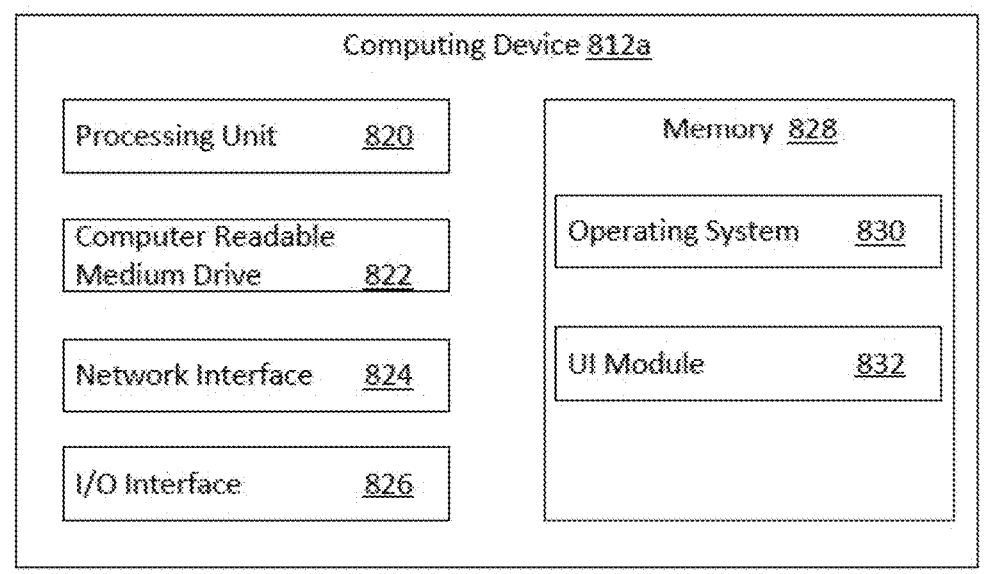

Turning now to FIG. 8, an exemplary system 810 for implementing the aforementioned disclosure is shown. The system 810 may include one or more computing devices 812a, 812b in communication with one another, as well as with a server 814 and one or more databases or other data repositories 816, e.g., via Internet, intranet, ethernet, LAN, WAN, etc. The computing devices also may be in communication with additional computing devices 812c, 812d through a separate network 818. Although specific attention is paid to computing device 812a, each computing device may include a processor 820, one or more computer readable medium drive 822, a network interface 824, and one or more I/O interfaces 826. The device 812a also may include memory 828 including instructions configured to cause the processor to execute an operating system 830 as well as a user interface module 832 for generating the user interfaces described herein.

Additionally or alternatively, the disclosure presented herein may be used as part of or in conjunction with a system such as the one described in the commonly-assigned U.S. patent application Ser. No. 16/657,804, filed Oct. 18, 2019, and titled "Data Based Cancer Research and Treatment Systems and Methods," the contents of which is incorporated by reference herein in its entirety.

Turning now to FIGS. 9-14, in another instance and as an alternative to the DNA metrics use case described above, the system may be used to derive an RNA-based similarity metric. In particular, the system may rely on whole transcriptome comparisons, i.e., a comparison of the expression information from all genes, among a cohort of patients.

In order to accomplish this analysis, each patient's expression information may be turned into a binary over-expression state. Then, the transcriptome data may be reduced or compressed in order to identify key factors gleaned from that data. The reduced or compressed data then may be used to compare patients, e.g., using a radar plot similar to those described above and shown in FIGS. 1, 2B, 4A, and/or 4B.

FIG. 9 illustrates exemplary normalized gene expression counts for a plurality of cancer patients. In the case of whole transcriptome comparisons, the data set may comprise information for 20,000 or more genes, although only a small handful of those are presented in FIG. 9 for the sake of clarity and brevity.

In order to provide relevant context to the expression counts, those values may be compared against some standardized or threshold values. For example, the gene expression counts may be compared against normalized gene counts taken from non-cancer tissues, exemplary values of which are provided in the table of FIG. 10. Also, it will be understood that different cancers overexpress different patterns of genes, so the normalized counts against which each patient's counts are compared may vary depending on the type of cancer being analyzed.

Each patient's gene expressions may be compared against these threshold values to determine whether, for each gene, they exceed those values. The analysis may be a binary one, where a value of 1 is assigned to those genes exceeding the cutoff and a value of 0 is assigned to those genes at or below the cutoff level. (In this example, a gene having the same expression as the cutoff is assigned a value of 0; alternatively, that gene may be assigned a value of 1). A result of this comparison may result in the N×G matrix M of over-expression states seen in FIG. 11.

Once the gene expressions have been converted to their compared values, the whole transcriptome data (again, about 20,000+ genes) may be compressed by selecting a number K of meta-genes that represent key analytical factors. Those factors may represent common patterns of over- and/or normal-expression across genes. The number of meta-genes may be variable but may be multiple orders of magnitude smaller than the total number of genes in the whole transcriptome data. For example, the number of meta-genes may be between about 5 and about 50, or between about 5 and about 25, or between about 5 and about 15, and in one specific embodiment may be about 7.

One of various analytical models may be chosen to determine the meta-genes. The analytical model may be, e.g., a latent Dirichlet allocation model, a mixed-membership model, or a grade of membership model that is connected to non-negative matrix factorization, where a goal of the model is to identify genes that correlate to clusters in cancer samples.

Factors within each model may be chosen so as to separate patients by over-expression differences across multiple genes, and one way to accomplish this is to weight genes differently. For example, the mere fact that a patient's gene is over-expressed or under-expressed may not be significant if that gene is always over-expressed or always under-expressed. Such genes may be given little or no weight, so as not to influence any factor. Additionally, if a gene over-expression state is variable and also not correlated with the over-expression state from other genes, that gene may be down-weighted if the model is designed to identify patterns of co-incident over-expression from multiple genes.

In one particular aspect, which may be relevant to either or both of the RNA analysis disclosed herein or a DNA analysis, the meta-genes may be a combination of genes that represent a genetic pathway, as that term is understood by those of ordinary skill in the relevant art. In particular, the system may include a database of one or more different genetic pathway names and the constituent genes that make up each of those pathways. The user interface may include a region with an interactive field permitting the user to select a desired pathway from a list of potential pathways. Additionally or alternatively, the user selection of a desired pathway using the graphical user interface may be an iterative process, whereby the user first selects a specific gene (e.g., by typing it into a search field, selecting it from a list of potential genes, or some other manner), upon which the interface refreshes to display to the user all pathways of which that gene is a part. If the desired pathway is identified at that stage, the user may be able to select it directly. Otherwise, the user interface may be configured to receive a second gene selection from the user, upon which the system analyzes the previous subset of pathways to determine those of which the second gene also is a part. The process may repeat until a user enters a gene that does not belong to any pathway, at which point the user may have to delete a selection of one or more previously-selected genes to see if any pathways match the broader search, or until a user enters sufficient information so as to be able to select a desired pathway. In this way, the radar plot that is generated may compare a reference patient with other patients relative to the desired pathway.

FIG. 12 provides a K×G latent overexpression matrix of factors derivable from the data shown in FIG. 11, and FIG. 13 illustrates how those factors are applied so as to summarize the over-expression states of FIG. 11, where the grayscale shading applied to the cell indicates whether that a normalized over-expression value is more similar to the first or section factor of FIG. 11 Although FIG. 12 shows two latent factors, it will be understood that the number of latent factors is a function of the extent of clustering in the cancer type and the available sample size to be able to detect them. Thus, an analysis relative to pancreatic cancer may have, e.g., 5 latent factors, lung cancer may have 7 latent factors, and breast cancer may have 9. In another aspect, brain cancer may have 9 latent factors, breast cancer may have 8, colorectal cancer may have 3, kidney cancer may have 9, lung cancer may have 10, ovarian cancer may have 3, and pancreatic cancer may have 2.

For N patients and K RNA meta-genes, FIG. 14 then provides an N×K patient factor matrix representing each patient's relative over-expression relative to each factor. It will be understood that the actual percentages for patients may be a wider, non-uniform distribution, as the number of factors increases, and as the likelihood that a patient will be overexpressed relative to only a handful of genes for each factor also increases.

Once this analysis has been performed, it may be possible to compare patients relative to one another so as to generate a radar plot similar to the ones discussed above and shown in FIGS. 1, 2B, 4A, and 4B. In one instance, similarity between patients may be determined by determining a sum of the absolute differences in proportions for each factor for each patient. Alternatively, the method also may involve determining which factors are more distinct than other factors, as a difference in proportions for more distinct factors may be more significant than a difference in proportion for relatively similar factors. One method of determining distinctness may be to measure how well the mixture proportions for patient A work for patient B and vice-versa, because two patients' transcriptomes may be far away if there is significant evidence that they cannot be swapped but close if there is little evidence that they cannot be swapped. In order to quantitatively measure this ability to swap mixture proportions may be to calculate a likelihood ratio for each pair of patients A and B, where that ratio is:

$$\frac{P(\text{over-expressions for }pA\text{ given properties for }pA) \times P(\text{over-expressions for }pB\text{ given properties for }pB)}{P(\text{over-expressions for }pA\text{ given properties for }pB) \times P(\text{over-expressions for }pB\text{ given properties for }pA)}$$

Formally, ratio may be calculated as:

$$L_{ij} = \log\left(\frac{l(\bar{e}_i \mid \pi_i) * l(\bar{e}_j \mid \pi_j)}{l(\bar{e}_i \mid \pi_j) * l(\bar{e}_j \mid \pi_i)}\right)$$

where $\bar{e}_i$ are overexpression calls and $\pi_i$ are the factor proportions for patient i.

$L_{i,j}$ then may be scaled, e.g., using a monotonic transform, to the interval [0, 1] so that a radar plot may be generated, where $L_{i,j}$ may represent a radial distance of patient j from reference patient i. Similar calculations may be performed for each of the other patients in the cohort to determine their radial distances, i.e., their similarity levels, relative to the reference patient. Using the techniques described above, the angular position of each patient j also may be determined, so as to generate the radar plot.

While the disclosure herein has been directed to the analysis of genetic mutations as enabling a comparison of a cohort of patients with various cancers, similar comparisons based on genetic mutations or other comparative criteria, including clinical, physical, and/or genomic patient characteristics, as well as diagnosis, treatments, and treatment efficacy may be used to evaluate patients with other disease states. For example, the method may be applied to evaluate a cohort of patients based on mental disorder disease states identified according to the details set forth in the commonly-assigned U.S. provisional patent application 62/882,466, filed Aug. 2, 2019, and titled "Data-Based Mental Disorder Research and Treatment Systems and Methods," the contents of which is incorporated by reference herein in its entirety. In particular, the present disclosure may be used with regard to one, some, or all of the genes identified in that application.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A method, comprising:

receiving a first dataset, the first dataset having at least a first, second, and third member, where the first, second, and third members are matched to a plurality of identifiers;

receiving a second dataset, the second dataset having a plurality of importance signifiers, where one or more of the plurality of importance signifiers are matched to one or more of the plurality of identifiers of the first dataset;

generating a third dataset based at least in part from the first and second dataset, the third dataset having the plurality of identifiers of the first dataset matched with a plurality of scaled importance factors;

generating, by a processing device, a fourth dataset based at least in part on the first, second, and third datasets, the fourth dataset having a measure of similarity between the first member and the second member, a measure of similarity between the first member and the third member, and a measure of similarity between the second member and the third member;

receiving a selection of the first member from a user;

identifying a first angular assignment for the second member and a second angular assignment for the third member, wherein the first and second angular assignments minimize a sum of squared error function and the second angular assignment indicates a similarity between the second member and the third member; and displaying, via a display operatively connected to the processing device, the first member at a focal point of a graphical user interface on a display, the second member at a first radial distance based on the measure of similarity between the first and second member and the first angular assignment, and the third member at a second radial distance based on the measure of similarity between the first and third member and the second angular assignment.

2. The method of claim 1, wherein the first member is an oncology patient, wherein a first identifier of the plurality of identifiers is a first genetic mutation, and wherein the plurality of importance signifiers include evidence of FDA-approved therapy for each gene and evidence of correlation to causing cancer for each gene.

3. The method of claim 2, further comprising:
processing first and second datasets and extracting clusters of interest.

4. The method of claim 2, further comprising calculating the measure of similarity between the first member and the second member by:
assigning a first value based at least in part on a number of gene mutations the first and second member have in common; and
modifying the first value by a second value based at least in part on a number of gene mutations the first and second member do not have in common.

5. The method of claim 1, wherein a first identifier of the plurality of identifiers is a normalized gene expression count exceeding a threshold value for a first gene.

6. The method of claim 5, wherein the plurality of importance signifiers includes the first gene being part of one or more first genetic pathways.

7. The method of claim 6, wherein the plurality of identifiers includes normalized gene expression counts exceeding a threshold value for at least a second gene.

8. The method of claim 7, wherein the plurality of importance signifiers includes the at least a second gene being part of at least one of the one or more first genetic pathways.

9. The method of claim 5, wherein the graphical user interface includes a selectable region configured to permit the user to select a first gene from among a plurality of genes or a genetic pathway from among a plurality of genetic pathways.

10. A system, comprising:
a display; and
a processor, the processor operatively connected to the display, the processor to:
receive a distance matrix for a plurality of patients and a patient of interest;
assign a radial distance value between the patient of interest and the other patients based on the distance matrix value for each patient of the plurality of patients;
generate an angular distance value for each patient and each other patient of the plurality of patients based at least in part on a measure of similarity between each patient;
minimize a cost function based at least in part on the angular distance value between each patient and each other patient of the plurality of patients, wherein minimizing the cost function comprises:
calculating a patient contribution to the cost function for a plurality of angular distance values; and
selecting the angular distance value with the smallest patient contribution;
generate a radar plot based at least in part on the assigned radial distance value and generated angular distance value of each patient; and
cause the display to display the radar plot.

11. The system of claim 10, wherein the distance matrix is derived from a comparison of one or more genetic mutations in the patient of interest and the plurality of patients.

12. The system of claim 11, wherein the measure of similarity is derived from a comparison of the one or more genetic mutations among the plurality of patients.

13. The system of claim 10, wherein the patient of interest is an oncology patient, wherein the distance matrix is derived from a comparative analysis of cancer type as between the patient of interest and the plurality of patients.

14. The system of claim 13, wherein the measure of similarity is derived, at least in part, from responses to treatment for each of the plurality of patients.

15. The system of claim 14, wherein responses include an indication of a type of treatment, favorable results to a given therapy, a percentage of remission after one or more time periods, and/or an indication of an existence or lack of adverse side effects.

16. A method, comprising:
receiving a first dataset, the first dataset having at least a first, second, and third member, where the first, second, and third members are matched to respective gene expression counts;
normalizing the respective gene expression counts relative to threshold values for each gene;
selecting one or more member-comparison factors;
identifying one or more meta-genes relevant to the one or more member-comparison factors;
comparing normalized gene expression counts for the one or more meta-genes for the first member against normalized gene expression counts for the one or more meta-genes for the second and third members to generate a second dataset representing each member's relative over-expression relative to each meta-gene,
receiving a selection of the first member from a user;
identifying a first angular assignment for the second member and a second angular assignment for the third member; and
displaying, via a display operatively connected to the processing device, the first member at a focal point of a graphical user interface on a display, the second member at a first radial distance based on the measure of similarity between the first and second member and the first angular assignment, and the third member at a second radial distance based on the measure of similarity between the first and third member and the second angular assignment.

17. The method of claim 16, wherein one of the one or more member-comparison factors is a specific type of disease state, the method further comprising:
receiving, via the graphical user interface, a user indication of the specific type of disease state from a user; and
selecting the meta-genes based on the user indicated disease state.

18. The method of claim 16, wherein the one or more member-comparison factors is a mutation of one or more genes in a genetic pathway, the method further comprising:
receiving, via the graphical user interface, a user indication of a specific gene from a user;
identifying one or more genetic pathways including the specific gene;
receiving, via the graphical user interface, a user indication of one of the one or more genetic pathways; and
selecting the meta-genes based on the user indicated genetic pathway.

19. The method of claim 16, wherein the one or more member-comparison factors is a mutation of one or more genes in a genetic pathway, the method further comprising:
receiving, via the graphical user interface, a user indication of one of the one or more genetic pathways from among a plurality of genetic pathways; and selecting the meta-genes based on the user indicated genetic pathway.

\* \* \* \* \*